United States Patent [19]
Ekenberg et al.

[11] Patent Number: 5,567,326
[45] Date of Patent: Oct. 22, 1996

[54] MULTISAMPLE MAGNETIC SEPARATION DEVICE

[75] Inventors: Steven J. Ekenberg, Mt. Horeb; Paula R. G. Brisco, Madison, both of Wis.

[73] Assignee: Promega Corporation, Madison, Wis.

[21] Appl. No.: 308,561

[22] Filed: Sep. 19, 1994

[51] Int. Cl.$^6$ .................................................. B01D 35/06
[52] U.S. Cl. ........................ 210/695; 210/222; 436/526
[58] Field of Search ................................. 210/222, 695; 436/526, 806; 435/173.9; 335/285; 422/101

[56] References Cited

U.S. PATENT DOCUMENTS

| | | | |
|---|---|---|---|
| 3,184,655 | 5/1965 | Brown ................................. | 335/285 |
| 3,700,555 | 10/1972 | Widmark et al. . | |
| 3,970,518 | 7/1976 | Giaever . | |
| 3,985,649 | 10/1976 | Eddelman ............................ | 210/695 |
| 4,018,886 | 4/1977 | Giaever . | |
| 4,190,524 | 2/1980 | Watson ................................. | 210/222 |
| 4,230,685 | 10/1980 | Senyei et al. . | |
| 4,267,234 | 5/1981 | Rembaum . | |
| 4,272,510 | 6/1981 | Smith et al. ........................ | 436/526 |
| 4,375,407 | 3/1983 | Kronick . | |
| 4,452,773 | 6/1984 | Molday . | |
| 4,508,625 | 4/1985 | Graham . | |
| 4,554,088 | 11/1985 | Whitehead et al. . | |
| 4,649,116 | 3/1987 | Daty et al. ........................... | 210/222 |
| 4,659,678 | 4/1987 | Forrest et al. . | |
| 4,710,472 | 12/1987 | Saur et al. . | |
| 4,738,773 | 4/1988 | Müller-Ruchholtz et al. . | |
| 4,978,610 | 12/1990 | Forrest et al. . | |
| 4,988,618 | 1/1991 | Li et al. . | |
| 5,186,827 | 2/1993 | Liberti et al. . | |
| 5,200,084 | 4/1993 | Liberti et al. . | |

FOREIGN PATENT DOCUMENTS

| | | | |
|---|---|---|---|
| 671930 | 10/1963 | Canada ................................. | 335/285 |
| 0317286A2 | 5/1989 | European Pat. Off. . | |
| 1026520 | 4/1966 | United Kingdom ................ | 335/285 |
| WO90/10716 | 9/1990 | WIPO . | |

OTHER PUBLICATIONS

R. R. Oder, *IEEE Trans. Magnetics*, 12 (1976) 428–435.
C. Owen and P. Liberti, *Cell Separation: Methods and Selected Applications*, vol. 4, Pretlow and Pretlow eds., Academic Press, New York (1987).

*Immunoassays for Clinical Chemistry*, pp. 147–162, Hunter et al., eds., Churchill Livingston, Edinborough (1983).

L. S. Hersh and S. Yaverbaum, *Clin. Chim. Acta*, "Magnetic Solid–Phase Radioimmunoassay," 63, pp. 69–72 (1975).

J. T. Kemshead and J. Ugelstad, *Molecular and Cellular Biochemistry*, "Magnetic separation techniques: their application to medicine," 67, pp. 11–18 (1985).

Product Information Sheet, Magnetic Particle Concentrator, DYNAL MPC 1, Product No. 12001, DYNAL, A.S., Oslo, Norway, 1991.

Product Information Sheet, BioMag Separators, Product Nos. 4101S, 4102S, and 4106S, Advanced Magnetics, Inc., Cambridge, Massachusetts.

Product Information Sheet, Magic™, magnetic immunochemistry method, Corning.

*Primary Examiner*—Matthew O. Savage
*Attorney, Agent, or Firm*—Grady J. Frenchick; Stroud, Stroud, Willink, Thompson & Howard

[57] ABSTRACT

Apparatus and methods for separating magnetically responsive particles from a nonmagnetic test medium in which the magnetically responsive particles are suspended. The separator comprises a container comprising, e.g., plurality of multiwell chambers, which hold the nonmagnetic test medium, one or more pins disposed substantially within the test medium, an external magnet for producing a magnetic field within the test medium. The external magnet is proximate the pins so as to create magnetic flux lines, magnetizing the pins and creating a magnetic field substantially parallel to the longitudinal axis of the pins thereof in the test medium. According to the method of the invention, the container holding the test medium is positioned in the separator, producing a magnetic field operative to cause the magnetically responsive particles to be attracted to and adhere to the pins and which is substantially parallel thereto. The nonmagnetic test medium is separated from the magnetized particles, which may conveniently be washed while adhered to the pins, and subjected to further analysis, preferably while on the pins. The apparatus and method are useful in separating various target substances from test media by means of substances coated on the magnetic particles which bind specifically to the target substance.

15 Claims, 5 Drawing Sheets

MULTISAMPLE MAGNETIC SEPARATION DEVICE

TECHNICAL FIELD

The present invention relates generally to magnetic separation apparatuses and methods in which magnetically responsive particles are used for isolating substances of interest from nonmagnetic test media. Specifically, the invention relates to a device wherein multiple samples can be magnetically separated and processed simultaneously, or sequentially, as desired.

BACKGROUND OF THE INVENTION

Laboratory and clinical procedures involving biospecific affinity reactions have dramatically affected health care and biological research. Such reactions are commonly employed in testing biological samples, such as blood or urine, for the identification, quantification, or both, of a wide range of target substances, for example, particular chemical substances that have been correlated or associated with various disease conditions. Biological entities such as cells, proteins, nucleic acid sequences, e.g., mRNA, and the like are preferred target substances as that term is used herein for utilization of the present invention.

Various methods are available for determining the above-mentioned target substances based upon complex formation or a binding reaction between the substance of interest, i.e., a ligand, and its specific binding partner which preferentially binds to the ligand and not to other constituents that may be present in the sample to be tested. In each instance, the occurrence or degree of target substance/binding partner complex formation is determinable.

Assays typically used in the art include immunoassays, hybridization assays and protein-ligand assays. Immunoassays are based upon the specificity of an antibody for an antigen. Hybridization assays are based on the specificity of complementary nucleic acid sequences, i.e., on the hybridization of nucleic acid probes with target nucleic acids. Protein-ligand assays depend on the affinity of a binding site on a protein for a specific ligand, e.g., streptavidin for biotin.

In each assay types, quantification of the target substance requires a physical separation of bound from free labeled ligand or labeled receptor. Bound/free separations may be accomplished, e.g., gravitationally by settling, or, alternatively, by centrifugation of finely divided particles or beads coupled to the target substance. Such particles or beads can be made magnetic and the bound/free separation step may be accomplished magnetically. Magnetic particles are well known in the art, as is their use in immune and other biospecific affinity reactions. See, for example, U.S. Pat. No. 4,554,088 and *Immunoassays for Clinical Chemistry*, Hunter et al., eds., Churchill Livingston, Edinborough (1983) pp. 147–162.

Magnetic particles ranging in size from 3 nm to many microns have been described in the patent literature, including, by way of example, U.S. Pat. Nos. 3,970,518; 4,018,886; 4,230,685; 4,267,234; 4,452,773; 4,554,088; 4,659,678; 4,978,610; and 5,200,084. Such small magnetic particles have proved to particularly useful in analyses involving biospecific affinity reactions. They are conveniently coated with biofunctional polymers, such as proteins, provide very high surface areas and give reasonable reaction kinetics.

These small magnetic particles generally fall into two broad categories. The first category includes particles that are permanently magnetized; and the second comprises particles that become magnetic only when subjected to a magnetic field, i.e., they are magnetically responsive particles, for example, paramagnetic particles.

The specific magnetic separation apparatus/method used for bound/free separations of target substance-bearing magnetic particles from test media will depend on the nature and particle size of the magnetic particle. Several magnetic separation devices are commercially available, which can readily remove micron size ferromagnetic particles from solution by employing relatively inexpensive permanent magnets. Examples of such magnetic separators are the MAIA Magnetic Separator manufactured by Serono Diagnostics, Norwell, Mass., U.S.A., the DYNAL MPC-1 manufactured by DYNAL, Inc., Great Neck, N.Y., U.S.A., and the BioMag Separator, manufactured by Advanced Magnetics, Inc., Cambridge, Mass., U.S.A. A similar magnetic separator, manufactured by Ciba-Corning Medical Diagnostics, Wampole, Mass., is provided with rows of bar magnets arranged in parallel and located at the base of the separator. This device accommodates 60 test tubes, with the closed end of each tube fitting into a recess between two of the bar magnets.

Such magnetic separators, however, have the disadvantage that the magnetic capture is accomplished by using positionally-fixed magnets placed external to the wall of the tube of the reaction vessel, and the magnetic particles are collected on the side of the tube. To release the particles, the vessels must be removed from the field of the magnets. This technique is very cumbersome when attempting to separate and process a large number of samples, e.g., ninety-six, as common in multiwell plates such as Microtiter™ plates, trademark product of Dynal.

Another approach is manifest in the MACS device made by Miltenyi Biotec GmbH, Gladbach, West Germany, which employs a column filled with a nonrigid steel wool matrix in cooperation with a permanent magnet. In operation, the enhanced magnetic field gradient produced in the vicinity of the steel wool matrix attracts and retains the magnetic particles while the nonmagnetic test medium passes through and is removed from the column. See, R. R. Oder, *IEEE Trans. Magnetics*, 12 (1976) 428–435; C. Owen and P. Liberti, *Cell Separation: Methods and Selected Applications*, Vol. 5, Pretlow and Pretlow eds., Academic Press, New York (1986).

It has been found, however, that use of the steel wool matrix of such prior art devices often gives rise to nonspecific entrapment of biological entities other than the target substances which cannot be removed completely without extensive washing and resuspension of the particles bearing the target substance. Moreover, the size of the column in many of the prior art devices requires substantial quantities of experimental materials, which pose an impediment to their use in performing various useful laboratory-scale separations. In addition, the steel wool matrix may be harmful to certain sensitive cell types.

Although the aforementioned prior art devices afford certain advantages in performing medical or biological analyses based on biospecific affinity reactions, the systems developed to date have not been entirely satisfactory for the above-mentioned reasons. Accordingly, it would be desirable to provide an apparatus which is of relatively simple construction and operation, which reduces loss of immobilized target substance and entrapment of nontarget substances, and employs standard multiwell plates and the like, so as to be of practical utility in conducting various laboratory-scale separations, particularly in protein ligand and hybridization assays.

SUMMARY OF THE INVENTION

The present invention provides a magnetic separation apparatus and methods capable of generating a magnetic field within a test medium to separate magnetically responsive particles, e.g., paramagnetic particles, from a nonmagnetic test medium. This invention relates specifically to magnetically responsive particles of a size which tends to settle out of a test medium, i.e., noncolloidal particles, and is not operable to separate particles of colloidal dimension.

As used herein, the term "target substance" refers to any member of a specific binding pair, i.e., a pair of substances or a substance and a structure exhibiting a mutual affinity of interaction and whereby the pair undergo a specific binding reaction. "Ligand" is used herein to refer to substances, such as biotin, antigens, haptens, proteins and various cell-associated structures, which are capable of being biospecifically recognized by and bound to a receptor. "Receptor" is used herein to refer to any substance or group of substances having a binding site and a high binding affinity for a given ligand, to the substantial exclusion of other substances. Among the receptors determinable via biospecific affinity reactions are biotin-binding proteins, antibodies (both polyclonal and monoclonal), antibody fragments, enzymes, nucleic acids and the like. The determination of one member of a biospecific binding pair is dependent upon its selective interaction with the other member of the pair. As used herein, the term "magnetically responsive" is meant to refer to materials that can be permanently magnetized and to temporarily magnetic materials, i.e., materials capable of being magnetized in the presence of a magnetic field but are not magnetic in the absence of such a field, such as paramagnetic materials.

The magnetic separator in accordance with the present invention advantageously can process a large number of samples, e.g., ninety-six, simultaneously, with quantitative recovery of the magnetically responsive particles, and at the same time quickly and easily release the magnetically responsive particles for, e.g., washing. Particle capture is typically greater than ninety-five percent. The separator apparatus is of relatively simple construction and operation, and magnetic separation in accordance with the present invention minimizes liquid transfers and the disposable items required to effect those transfers. The practice of the invention permits a high level of operating efficiency, i.e., of separation efficiency, which enables the efficient and effective separation of target substance-bearing magnetically responsive particles from a test medium, while at the same time permitting at will capture and release of the particles.

The foregoing, and other advantages of the present invention, are realized in one aspect thereof in a magnetic separator comprising a magnetic field-directing element, preferably in the form of one or more rigid magnetically responsive elements immersible in a test sample containing magnetically responsive particles having a linear dimension of about 500 nm to about 25 µm, and a permanent magnet external to the test sample and proximate the element. The magnet is configured and disposed to generate magnetic flux lines collinear with the element; thus, inducing, when the element is immersed in the test sample, a magnetic field such that the particles are attracted to the element. The magnet is preferably positioned above the elements and above the test sample. The magnet is also preferably removable, i.e., it is positionable to capture the magnetically responsive particles, but at the same time can be removed to release the particles. This removability is a highly advantageous feature of the present invention.

The magnetically responsive element is suitably rigid and, for example, cylindrical in shape, such as a pin or a rivet, and comprises a paramagnetic material. The magnetically responsive particles also suitably comprise a paramagnetic material.

In the illustrated embodiment, the separator includes a nonmagnetic separation chamber for performing the desired separation, i.e., for receiving the test samples which contain magnetically responsive particles. The chamber includes a base and a plurality of reaction sites disposed on the base in spaced-apart positions. Each of the reaction sites comprises a test sample containing the magnetically responsive particles having a pair of substances, which undergo a specific binding reaction with each other, bound to the surfaces of the particles. The separation chamber is suitably a multiwell plate, e.g., a Microtiter™ plate.

The element of the separator in accordance with the present invention also suitably includes a plurality of magnetically responsive elements which are held in an element plate. The element plate suitably has a bottom side and a top side and a plurality of bores therethrough for receiving and holding the plurality of elements. Each of the elements has a first end and a second end. The first end projects from the bottom side of the element plate and into the separation chamber, while the second end projects from the top side of the element plate. The element plate holding the plurality of elements is positioned outside and above the separation chamber such that the first ends of the elements are immersible in the test samples.

In the illustrated embodiment, the magnet in accordance with the present invention suitably comprises a pack of individual magnets which are substantially configured in single plane positioned perpendicular to the longitudinal axis of the elements and proximate the second ends of the elements. The individual magnets are arranged in an array such that, when the magnet pack is positioned on the top side of the element plate, there are four elements circumferentially proximate each individual magnet.

In a further aspect, the invention is a method of separating magnetic particles from nonmagnetic components of a test sample using the separator of the present invention. The method includes dispersing magnetically responsive particles that have a linear dimension in the range of about 500 nm to about 25 µm in a test sample which is held in one or more of the wells of the separation chamber. The magnetically responsive elements are positioned in the magnetic separator, with the elements immersed within the test samples, i.e., one element immersed in each test sample. The separator brings an external magnetic field to bear on the test samples and the elements, preferably from a position above the test samples and above the elements, producing a magnetic field within the test sample, which causes the magnetically responsive particles to be attracted toward the magnetized elements and to become adhered thereto. Thereafter, the nonmagnetic test medium may be removed from the separator while the magnetic particles are retained on the elements and are subjected to further processing, as desired. The external magnetic field is advantageously removed so that the particles are readily released for washing. The separator also permits the particles to be readily transferred to different plates for different reaction conditions. Accordingly, this method substantially reduces the processing time required for, and thus the cost of, bioanalytical testing.

The magnetically responsive particles comprise a receptor capable of specific binding to a target substance of interest in the test medium to form receptor particle conjugates. Such conjugation permits detection of target substances using the apparatus of the invention as described herein. This method of detecting a target substance constitutes another aspect of the invention.

Other advantages and a fuller appreciation of the specific attributes of this invention will be gained upon an examination of the following drawings, detailed description of preferred embodiments, and appended claims. It is expressly understood that the drawings are for the purpose of illustration and description only, and are not intended as a definition of the limits of the invention.

BRIEF DESCRIPTION OF THE DRAWINGS

The preferred exemplary embodiment of the present invention will hereinafter be described in conjunction with the appended drawing wherein like designations refer to like elements throughout and in which.

DETAILED DESCRIPTION

The present invention relates broadly to magnetic separation devices for separation of magnetic particles from nonmagnetic media. However, the present invention is particularly well-suited for use in separating biological substances of interest in various laboratory and clinical procedures involving biospecific affinity reactions. Accordingly, the present invention will now be described in detail with respect to such endeavors; however, those skilled in the art will appreciate that such a description of the invention is meant to be exemplary only and should not be viewed as limitative on the full scope thereof.

The present invention provides a magnetic separation apparatus and methods having particular utility in separating magnetically responsive particles from nonmagnetic media. The invention is characterized by an ability to magnetically separate multiple samples simultaneously, yet using only a single external magnetic source, preferably in the form of a magnet pack, that induces a magnetic field in magnetically responsive elements placed directly in the test medium. These attributes are achieved through a novel combination of structural features and physical parameters.

The method in accordance with the present invention utilizes particles that are magnetically responsive and that comprise a receptor capable of binding the target substance of interest in the test sample. After the receptor binds the target substance, the magnetic separator removes the magnetically responsive particles bound with substance of interest from the test medium via the application of a magnetic field.

Such biospecific affinity reactions may be employed in testing biological samples for the determination of a wide range of target substances, representative of which are cells, cell components, cell subpopulations (both eucaryotic and procaryotic), bacteria, parasites, antigens, specific antibodies, specific biological factors, such as proteins, vitamins, viruses and specific nucleic acid sequences, as in the case of gene probe analysis. Thus, the magnetic separation apparatus and method of the invention has application in cell separations for the analysis or isolation of cells including, by way of example: T-cells from a T-cell lymphoma cell line; B-cells from a B-cell lymphoma cell line; CD4 positive cells from leukocytes; and lymphocytes from leukocytes.

The methods in accordance with the invention may also be used for immunospecific isolation of monocytes, granulocytes and other cell types; removal of rare cells; depletion of natural killer cells; determination of reticulocytes; and assays for neutrophil function, e.g., for determining changes in membrane potential, performing oxidative burst analysis, phagocytosis assays and opsonization studies.

Further, the present magnetic separation apparatus and method may be used, by way of example, for generation of single-stranded DNA probes, for isolation of specific proteins, bacteria and cell organelles, for immunoassay, DNA purification, DNA binding protein purification, mRNA purification, cell sorting, purification of biotinylated PCR products and antibody-paramagnetic paramagnetic particle:antigen and antigen-paramagnetic particle:antibody isolations.

Magnetically responsive particles in accordance with the present invention are suitably composed of ferromagnetic or paramagnetic materials such as, for example, metals (e.g. iron, nickel or cobalt), metal alloys (e.g., magnetic alloys of aluminum, nickel and cobalt) and metal oxides (e.g., $Fe_3O_4$ or $Fe_2O_3$). The preferred material is the paramagnetic ferric oxide.

The magnetically responsive particles are also suitably provided with a nonmagnetic polymeric matrix or coating. As such, a crystalline core of magnetically responsive material is surrounded by molecules which may be physically absorbed or covalently attached to the magnetically responsive core. For example, preferred are particles of an iron oxide core coated with silane or styrene. The coatings are applied by known standard coupling protocols, typically through the use of functional groups such as $NH_3$ or COOH groups. The magnetically responsive particles are further surrounded by receptor molecules or molecular probes depending on the type of ligand to be separated.

The preferred magnetically responsive particles for use in carrying out this invention are particles having a size in the range of about 500 nm to about 25 μm, i.e., noncolloidal particles that will eventually sediment out under the effects of gravity. Magnetically responsive particles having the above-described properties are, for example, streptavidin-coated iron oxide cores which are commercially available as Streptavidin MagneSphere® paramagnetic particles, trademarked product of Promega Corporation, Madison, Wis.

For cell separations, the test medium is typically prepared from appropriately prepared body fluids, such as blood, urine, sputum or secretions. It is preferable to add the magnetically responsive particles to the test medium in a buffer solution. A suitable buffer solution for this purpose comprises a phosphate-buffered saline. The buffer solution should be isotonic, with a pH about 7. The target substance may be added to the test medium before, after or simultaneously with introduction of the magnetically responsive particles. However, for hybridization assays, e.g., mRNA purification, it has been found that the magnetically responsive particles are suitably added to the target substance after the hybridization reaction occurs. This method is the subject of co-pending application of the inventors, the contents of which are incorporated by reference. The test medium is usually incubated to promote binding between the receptor and any ligand of interest present therein. Incubation is typically conducted at room temperature, at a temperature slightly above the freezing point of the test medium (i.e., 4° C.) or at elevated temperatures (e.g., 70° C.). The period of incubation is normally of short duration (i.e., about 5 to 15 minutes).

After binding of the receptor to the substance of interest is allowed to occur, magnetic separation of the magnetically responsive particles from the test medium is performed using the apparatus and methods of the present invention. The test medium disposed in a container is subjected to an externally applied magnetic field, whereby a magnetic flux is generated within the test medium. In accordance with a preferred embodiment of the invention, a rigid, substantially linear magnetically responsive element, e.g., a pin or rivet, is immersed in the test medium to direct the magnetic field to the test medium, so as to cause the magnetically responsive particles to migrate toward the surface of the magnetized pin to which they adhere, rendering them easily separable from the test medium.

A suitable element or pin may comprise a temporary magnet such as an electromagnet or a magnetizable material (e.g., steel) that is a material that can be magnetized by contact with a permanent magnet, e.g., by contacting the pin with a permanent magnet. In the illustrated embodiment, a pin composed of stainless steel is preferred. Such stainless steel pins are suitably treated for rust prevention by hardening and flaming to remove any iron from the surface of the pins.

The magnetic field external to the container of the test medium is suitably generated by a permanent magnet. In the illustrated embodiment, twenty-four substantially cylindrical magnets, 0.6 inch in diameter and ¼ inch in height, are suitably arranged in a single plane configuration. Most preferred magnets are rare earth Neodymium Iron Boron magnets available from Jobmaster Magnets Inc., Baltimore, Md., U.S.A. These magnets are sandwiched between nonmagnetic panels, e.g., polymeric material, to form the planar magnet pack. Unlike many prior art magnetic separators, the magnet pack is advantageously readily removable, yet can be readily placed in appropriate contact with the pins to produce the necessary magnetic field. Such magnetic arrangement possesses the necessary field strength and size requirements for magnetizing the pins.

Reference is now made to FIGS. 1–11 depicting a preferred embodiment of a magnetic separator in accordance with the present invention, and generally designated as reference numeral 20. The separator 20 includes an array 22 of containers 24 for holding a test medium 26, a plurality of magnetically responsive metal elements or pins 28, an element or pin plate 30 for holding the elements or pins 28, a base 32 for holding the containers 24, and a planar magnet pack 34 positioned above and perpendicular to the longitudinal axis of containers 24 and pins 28.

Figure 2:
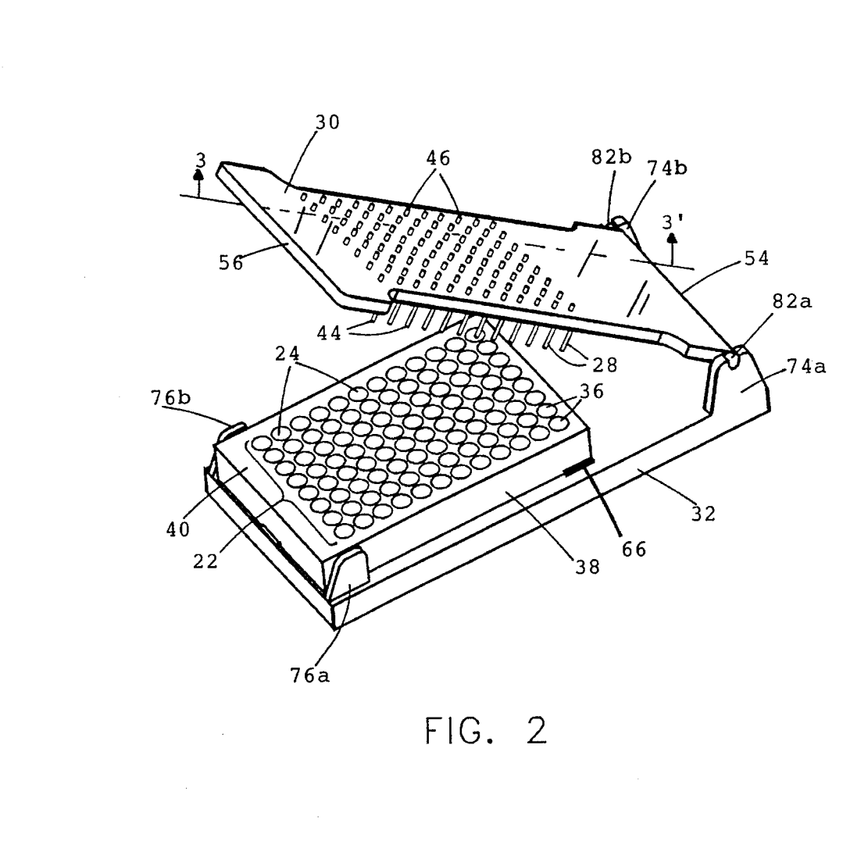
FIG. 2 is a perspective view of the magnetic separator of FIG. 1 illustrating the positioning of the test medium container plate and the hinged element plate.

As shown in FIG. 2 (and schematically in FIGS. 11), the container 24 used to hold the test medium 26 may be, for example, substantially cylindrical in shape with an open top 36 to receive the test medium 26 and a closed bottom 37. The array 22 of containers 24 defines a separation chamber 40. In this embodiment, the containers 24 are cylindrical vessels that are integral to the separation chamber 40. Separation chamber 40 includes a base 38 which serves as a connector for interconnecting adjacent containers 24 in the array 22. If desired, the base 38 may be scored or provided with weakened lines (not shown) intermediate the containers to enable separation of the individual containers 24. In the illustrated embodiment, each container 24 is suitably a micro well and most preferably, the array 22 comprises a multiwell plate with ninety-six containers or wells in twelve rows by eight rows. Such arrangement and number of wells is in common usage, e.g., a Microtiter™ plate, although it is understood that the array of interconnected containers may be of any number, including single containers or shaped tubes. All of the containers or wells may be used concurrently in the present method, thus permitting many separations of magnetic particles from test media to be carried out simultaneously or sequentially, as desired.

In operation, when the magnetic pack 34 is placed on top of the pin plate 30, the pins 28 are immersed in the test medium 26 creating a magnetic field in the area of the test medium. The pins 28 are anchored in pin plate 30 and form a pin array 42, as described hereinafter. Each pin 28 has one end 44 insertable into a container 24 (and into test medium 26). The other end 46 of each pin 28 is attached to, penetrates and protrudes from pin plate 30.

Pins made from any of various nonmagnetic but magnetically responsive materials may be employed in the magnetic separator in accordance with the present invention. The pin(s) may be of greater diameter than standard gauge wire, preferably having a diameter of between about 0.5 mm and 2 mm and a length of about 6 mm to 15 mm. A shorter pin is preferable to decrease loss of magnetic field strength. The pin or pins are illustrated as substantially rigid and, for example, cylindrical with flat, blunt ends or termini, similar to a common rivet or wire, but may assume virtually any shape that satisfies the condition that the pins are capable of being substantially immersed within the test medium.

Figure 11:
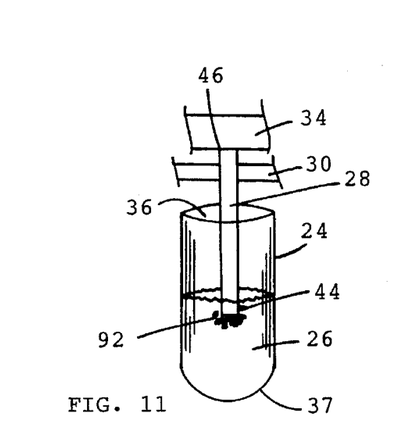
FIG. 11 is a schematic side view of a single container, pin and magnet illustrating the magnetically responsive particles adhering to the magnetized pin.

The pin configuration provides an ample surface area for adherence of the magnetized particles. An advantage of the magnetic separator of the invention, when utilized under the conditions described herein, is that by appropriately regulating the quantity of particles and the volume of the test medium, the particles tend to deposit substantially uniformly at the terminus the pin surface in contact with the medium when the magnetic field is applied as best seen in FIG. 11.

Figure 1:
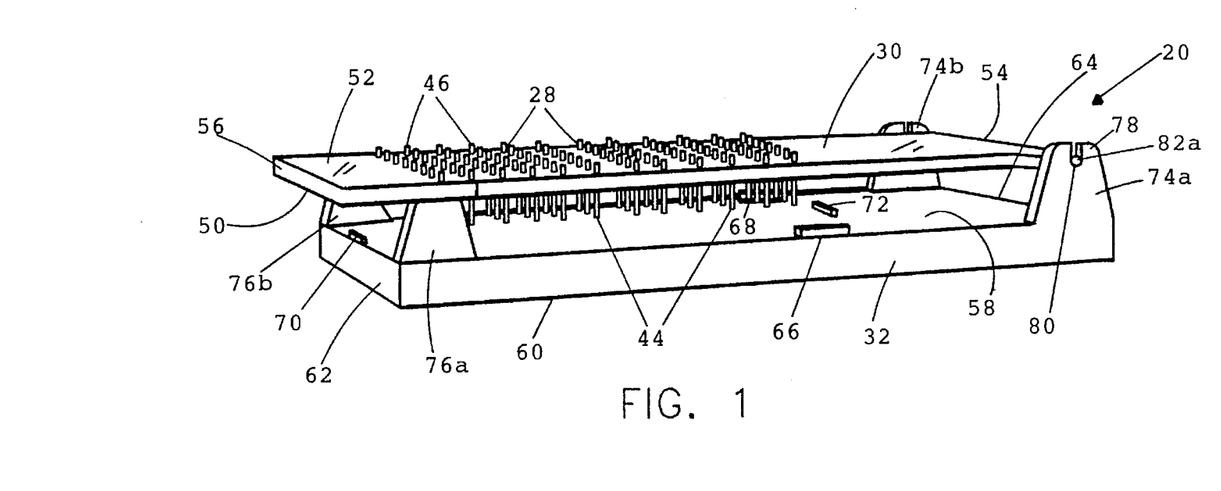
FIG. 1 is a perspective view of the magnetic separator in accordance with the present invention illustrating the hinged element plate and base.
Figure 3:
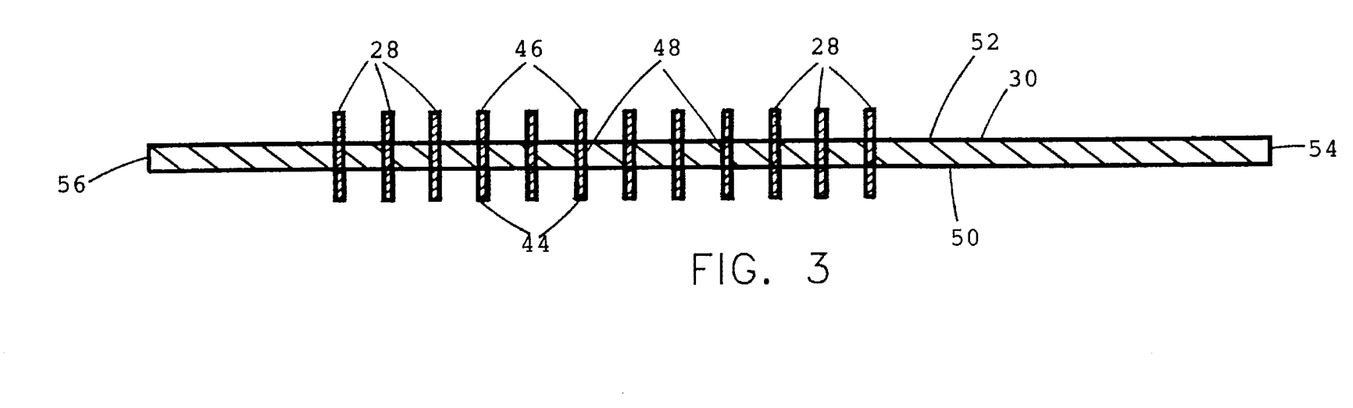
FIG. 3 is a sectional view taken through line 3—3' of the element plate of FIG. 2.
Figure 4:
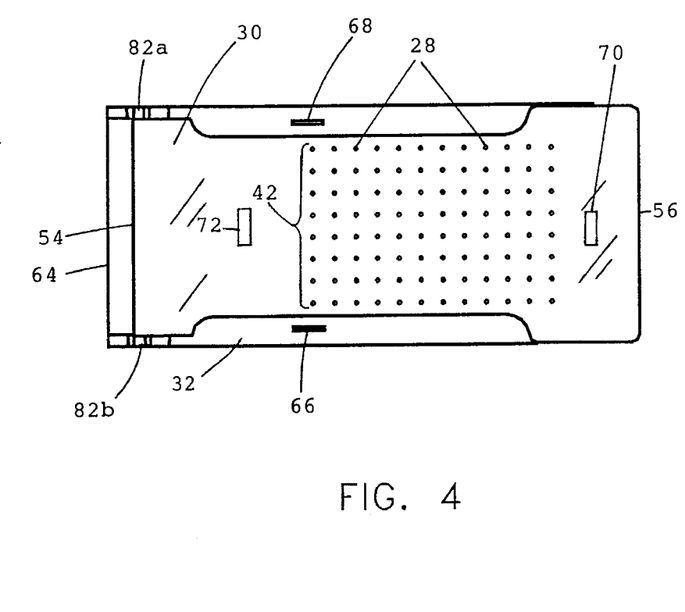
FIG. 4 is a top view of the magnetic separator of FIG. 1.

The pin plate 30, as best seen in FIGS. 1 and 3, is preferably nonmagnetic and transparent. The pin plate may be fabricated from various polymeric materials, for example, polycarbonate, polystyrene or Plexiglass®.

The plate 30 supports the pins 28 in a fixed position and also serves as a cover for the open top 36 of containers 24.

Pin plate 30 has a plurality of holes or bores 48 therethrough, each hole 48 receiving and snugly holding a pin 28. Pin plate 30 is substantially rectangular in shape, having opposing faces, 50 and 52, and ends 54 and 56. Face 50 faces and covers open ends 36 of containers 24. End 44 of each pin 28 projects from face 50 of pin plate 30, while end 46 of each pin projects from face 52.

Figure 7:
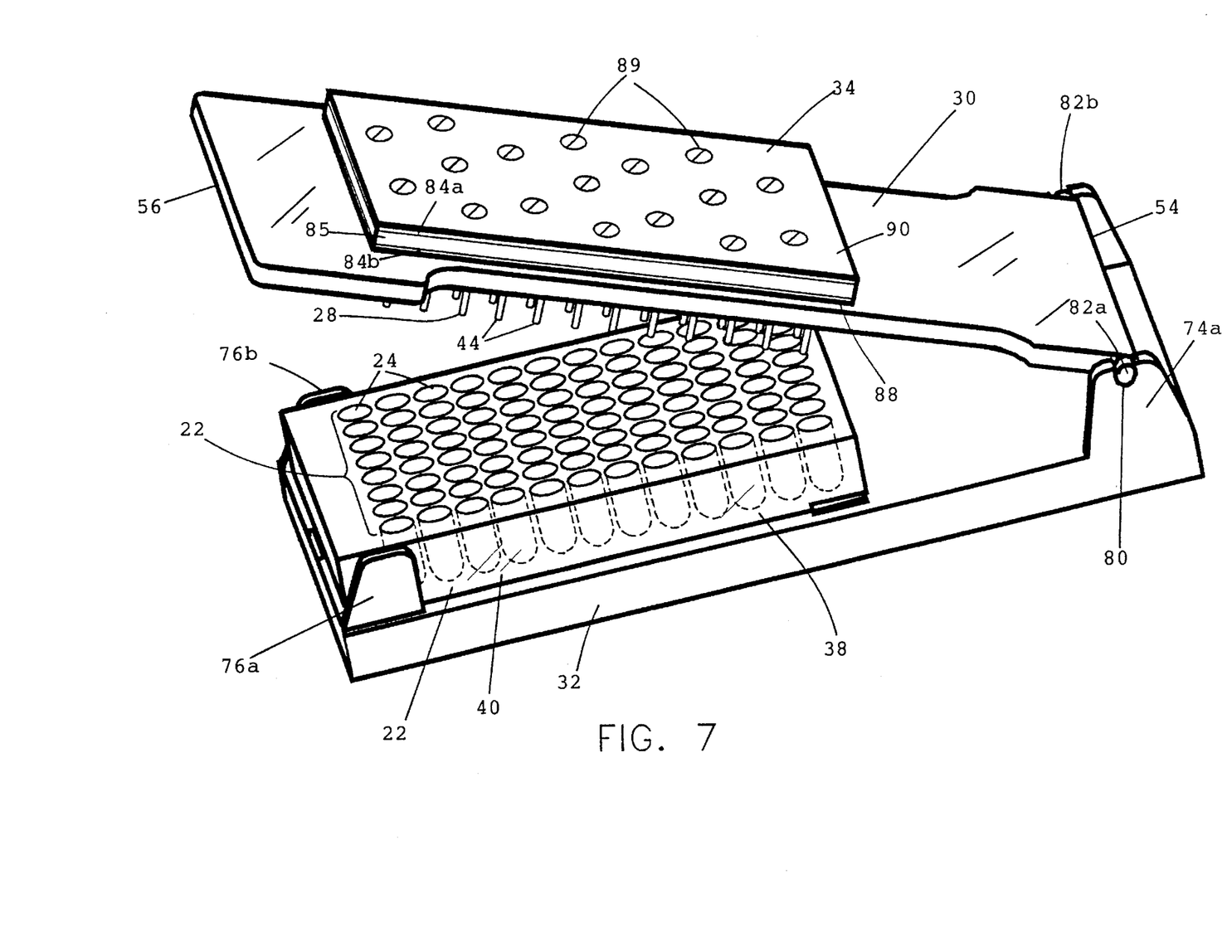
FIG. 7 is a perspective view of the magnetic separator illustrating the raising (and lowering) capability of the element plate and external magnet.

In the illustrated embodiment, as best seen in FIGS. 2 and 7, end 54 of pin plate 30 suitably is hingedly attached to base 32. Base 32 is substantially rectangular in shape, having opposing faces 58 and 60, and opposite ends 62 and 64. Face 58 of base 32 supports separation chamber 40 and has four guides or ridges 66, 68, 70 and 72 which are spaced apart and dimensioned for positioning chamber 40 in base 32. Guides 66 and 68 protrude upwardly from opposite sides of base 32. Guide 70 protrudes upwardly from end 62 while guide 72 protrudes from base 32 at a distance from end 62. It is understood that other aligning/positioning techniques, e.g., a relief area corresponding to the size of the separation chamber (e.g., a multiwell plate), can also be used.

End 64 of base 32 has two hinges, 74a and 74b, disposed on opposite sides of end 64 for plate 30. Hinges 74a and 74b are substantially arcuate in shape and each has a top 78 with a centrally disposed furrow or channel 80. End 54 of plate 30 has a pair of opposing pins or rods 82a and 82b extending from each side of plate 30. Channels 80 of base 32 receive rods 82a and 82b of plate 30 completing the hinges 74a and 74b. End 62 of base 32 also include additional guides or ridges 76a and 76b, extending upwardly, serving as guides for plate 30 opposite hinged end 64. Guides 76a and 76b are similarly shaped and dimensioned to hinges 74a and 74b.

Figure 5:
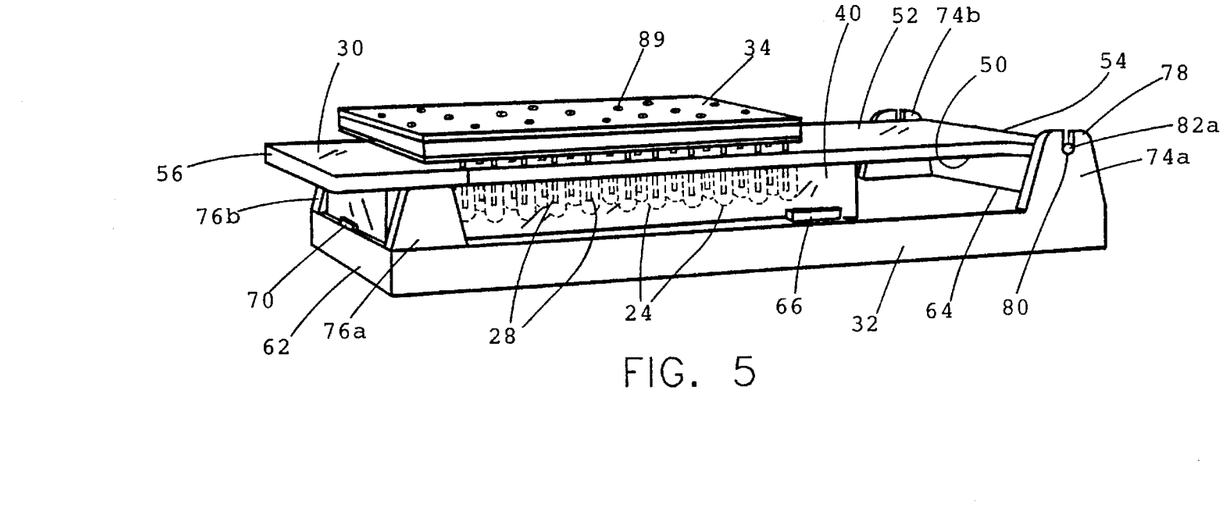
FIG. 5 is a side view of the magnetic separator with the external magnet in place.
Figure 6:
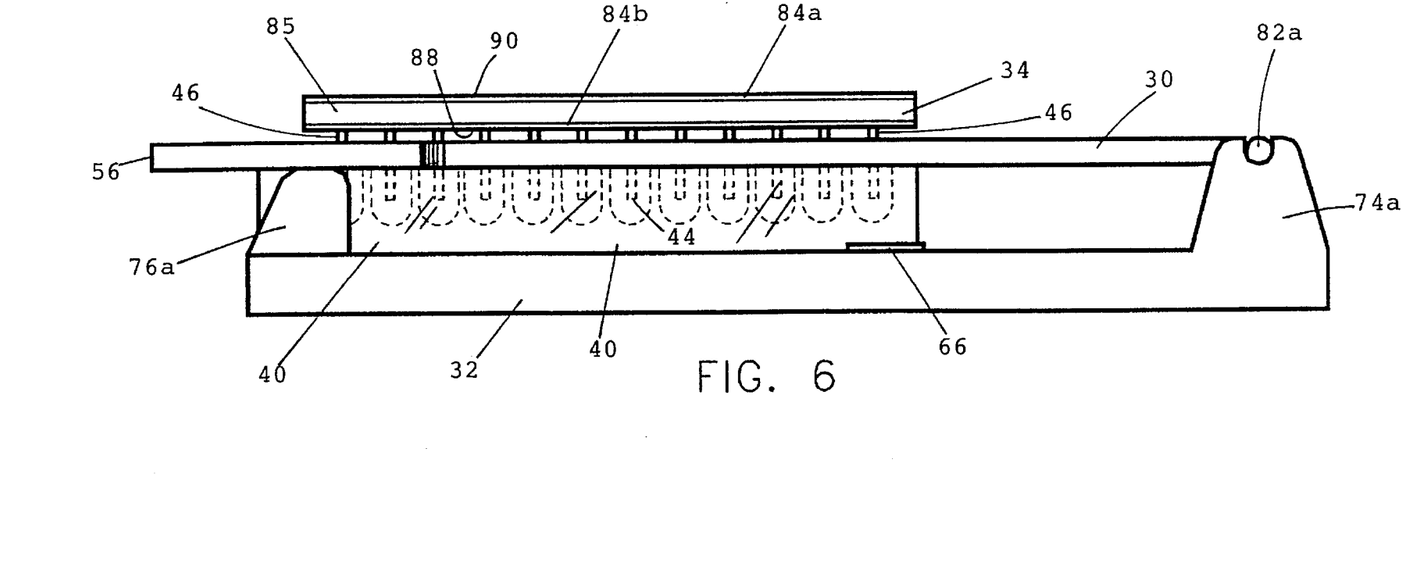
FIG. 6 is a side view of the magnetic separator with external magnet in place.
Figure 8:
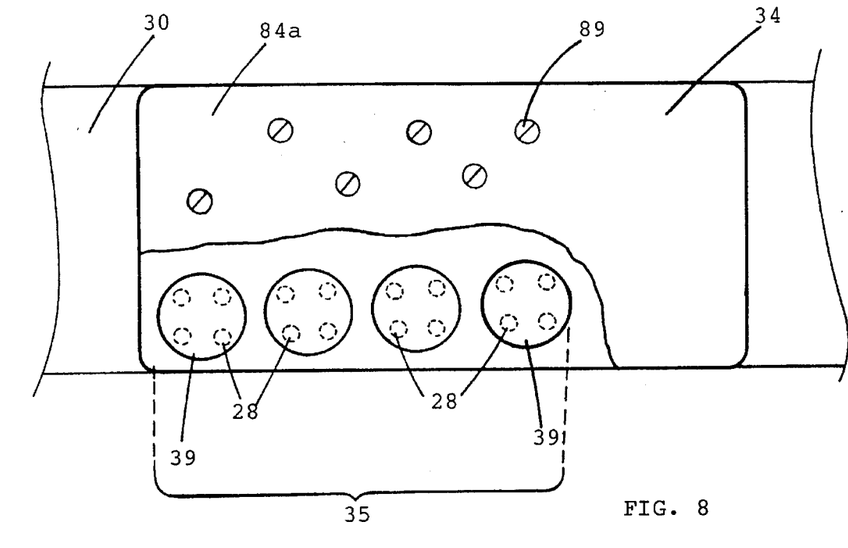
FIG. 8 is a partial cutaway top view of the external magnet pack with the elements of the element plate shown in phantom.
Figure 9:
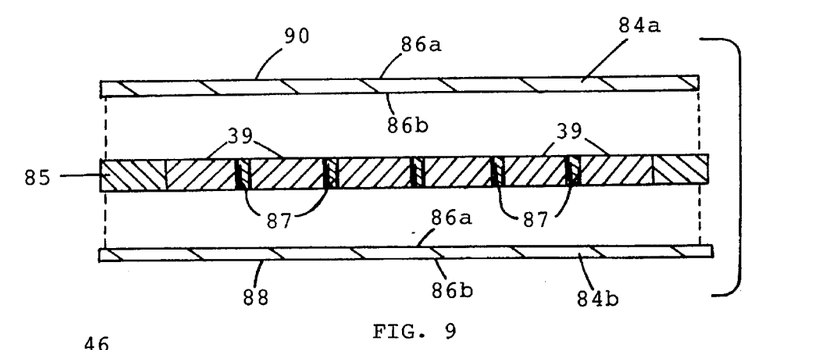
FIG. 9 is an exploded side sectional view of the magnet pack in accordance with the present invention.

In the embodiment of FIGS. 1–11, a magnetic field is achieved in the test medium 26 by the magnet pack 34. The pins 28 of a magnetically responsive material are magnetized by magnet pack 34. The magnet pack 34 is removably positioned above the array 22 of containers 24 and proximate the ends 46 of the pins 28. As shown in FIG. 5, induction of a magnetic flux in the test medium 26 is provided by external magnet pack 34. As best seen in FIG. 8, magnet pack 34 suitably includes an array 35 of individual magnets 39. In the illustrated embodiment, magnet array 35 includes six rows by four rows of individual magnets 39. Magnet array 35 is conveniently formed by disposing individual magnets 39 in a magnet holder 85 which is configured to have bores or holes 87 for receiving and holding magnets 37. Magnetic pack 34 is positioned above container array 22 and pin array 42 such that individual magnets 39 are positioned above pins 28 and the openings of containers 24. As best seen in FIG. 8, pins 28 are positioned such that one magnet 39 contacts four pins 28.

Array 35 of individual magnets 39 is suitably covered and held in place by providing cover plates 84a and 84b to form a sandwich-type arrangement of magnet holder 85 and plates 84a and 84b. Magnet cover plates 84a and 84b each have opposing faces 86a and 86b. Plates 84a and 84b are suitably fastened together with, for example, screws 89, thus forming opposing faces 88 and 90 of magnet pack 34. Plates 84 and holder 85 are suitably constructed of a polymeric material, e.g., ABS. This sandwich-type configuration defines a substantially rectangular and planar appearance to magnet pack 34. When magnet pack 34 is positioned above containers 24 and pin plate 30, face 88 contacts ends 46 of pins 28 and magnet pack 34 magnetically induces pins 28, i.e., magnetizing pins 28.

The energy produced by the external magnet pack 34, (i.e., the array of individual magnets 39) should be great enough to induce a magnetic field by means of the pins 28 within the containers 24 and within the test medium 26. The maximum external energy of the individual magnets of array 35 is suitably in a range of between about 27M Gauss-Oersteds (MGO) and about 35 MGO, and preferably about 35 MGO.

The pins 28 are preferably oriented so that the direction of the magnetic field of the magnets 39 is substantially along the longitudinal axes of the pins 28, thereby optimizing the magnetic field generated within the test medium 26.

Figure 10:
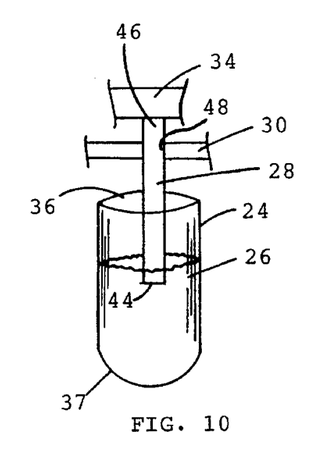
FIG. 10 is a schematic side view of a single container, pin and magnet, all in accordance with the present invention.

FIGS. 10 and 11 show a preferred positioning of a pin 28 in a container 24 relative to plate 30 and magnet pack 34. The pins 28 should not touch an inner wall of the container in order to avoid trapping of the target substance between the pins and the wall. In addition, the pins 28 are preferably equidistant from the walls; this arrangement substantially equalizes the distance between the magnetic particles and the closest pin surface. FIG. 11 illustrates the attraction and adherence of magnetically responsive particles 92 to pin 28.

To effect separation of the magnetically responsive particles 92 from the test medium 26 using the magnetic separator apparatus in accordance with the present invention, pin plate 30 is raised from containers 24 once the test medium 26 has been subjected to the magnetic field for a sufficient time to cause the magnetically responsive particles 92 to migrate and adhere to the ends 44 of pins 28 submerged in the test medium. The magnetically responsive particles 92 remain adhered to the pins 28 while the non-magnetic components of the test media 26 will be removed with the containers 24. A similar array 22 of containers containing a buffer, a rinse, or other fresh solution may then be positioned in the base 32 to immerse the pins in the fresh solution for rinsing or other processing purposes. If it is desired to resuspend the magnetic particles in the liquid reagent, the magnet pack is simply removed from the top of the pin plate. The magnetic particles are dislodged from the pins and resuspended in the liquid reagent, e.g., to facilitate analysis. In addition, the adherence of the magnetic particles to the pin is maintained to some extent even if the pin is removed from the magnetic field before further reaction with, or treatment of the particles. It is noted that a certain amount of residual hysteresis remains in the pins even after removal of the magnet pack; however, the surface tension of the solution when raising and lowering the pins is typically sufficient to strip the particles from the pins. The removable magnetic source, i.e., the magnet pack, permits capture and release of the particles at will.

The ability to retain and release the magnetic particles at will is of considerable utility as it permits any number of processing steps in which some require the particles to be immobilized and others to be resuspended. For example, in some cases, certain operations such as washing or rinsing the target substance, e.g., cells or labeled components of a reaction mixture, are more efficiently carried out with the particles immobilized. Thereafter, various analytical procedures, including quantitative determinations, may even be performed on the magnetically immobilized particles. In other cases, where the target substance is to be subjected to further processing, resuspension is more appropriate. Such removability of the magnetic source provides advantages not found in fixed magnetic source devices wherein the test vessels must be moved to remove the magnetic field.

Performing the magnetic separation method of the invention batchwise or in a steady-state system, as described above, instead of in a flow-through system, e.g., column systems, has certain advantages. Immobilized magnetically responsive particles bearing the target substance are not dislodged due to collisions with other particles. Moreover, batchwise operation eliminates dislodgement of immobilized magnetically responsive particles due to shear forces produced by a flowing test medium. In other words, the adherence of the magnetically responsive particles to the pin is sufficiently strong to permit washing, secondary reactions, and interactions with other reagents to occur without appreciable dislodgement of the magnetically responsive particles from the pin. At the same time, if desired, the particles are readily and easily dislodged by simple removal of the magnet pack.

In general, the magnetically responsive particles are relatively easily separated from the pin after removal from the magnetic field. The particles may be separated by contacting the pin with a modified buffer solution wherein the surface tension of the solution is sufficient to strip the particles from the pin. Alternatively, the particles may be collected as they are dislodged from the pin, or oscillating magnetic fields can be employed to demagnetize the pins as well as create forces on the particles.

The following examples further describe in some detail the manner and process of making and using the present invention and set forth the best mode contemplated by the inventors for carrying out the invention, but are not to be construed as limiting the invention. All temperatures given in the examples are in degrees Celsius, unless otherwise indicated.

EXAMPLE 1

Treatment and Preparation of Pin Array

The pin array was treated in 1N sodium hydroxide for two minutes before use. The pins were then rinsed with deionized $H_2O$.

The pins in accordance with the present invention are reusable. For cleaning the pins after each use, pins can be washed in standard laboratory detergent using a cleaning brush. This is followed by the sodium hydroxide treatment described above. Alternatively, the pins can also be autoclaved to sterilize and remove nucleases and nucleic acids.

EXAMPLE 2 mRNA Purification-Tissue Sample

To process a 20 µl sample of tissue, β-mercaptoethanol (BME) was added to the guanidine thiocyanate (GTC) extraction buffer so that the final BME concentration was 2%. A tissue sample solution was prepared of 2.5 mg of tissue per 20 µl of GTC/BME. The tissue preparation was mechanically homogenized with an Omni-µH homogenizer fitted with interchangeably sterile disposable rotor-stator generators, and homogenized until no visible tissue mass remained.

20 µl of the homogenized preparation were transferred to each well of a multiwell plate such as a Microtiter™ plate. To each well of the plate, 40 µl of prewarmed (70° C.) hybridization buffer containing 1% BME and 3 pMol of biotinylated oligo(dT) were added and an incubation at room temperature for five minutes was effected.

To each well, 35 µl of blocking or masking particles were then added and the plate sealed. Centrifugation was effected at 1700×g (3400 RPM in a rotor where r=13.29 cm; RCF= 1716) using microplate carriers for ten minutes. Blocking or masking particles are the subject matter of commonly owned, copending application entitled "High Efficiency Method of Isolating Target Substances using a Multisample Separation Device," which application is incorporated by reference herein. Precipitated proteins and insoluble cell material are trapped beneath the pellet of blocking particles.

While centrifuging, 60 µl of magnetically responsive particles (Streptavidin MagneSphere™ Paramagnetic Particles ("SA-PMPs"), Promega Corporation, Madison, Wis., U.S.A.) per sample were placed in a vial and washed three times with 0.5×SSC containing 10 µg/ml bovine serum albumin (BSA) by repeatedly magnetizing and decanting the supernatant. The particles were then resuspended in the original volume of 0.5×SSC containing 10 µg/ml BSA. 60 µl of particles were placed in each well of the plate and the admixture was incubated for two minutes at room temperature.

The multiwell plate was then placed into the base of the magnetic separator of the present invention. The hinge pins of the pin plate were positioned in the channels of the hinges of the base and the pin plate was carefully lowered, immersing the pins into the wells of the microtiter plate. The external magnet pack was then placed on the top side of the pin plate, contacting the pin ends and the admixtures were incubated until the magnetic particles were cleared from the lysate, typically about 90 sec to 2 min.

The pin plate and magnet were then raised to about a 45° angle and the multiwell plate containing the cell lysates was removed and replaced with a fresh plate containing 165 µl of 0.5×SSC containing 10 µg/ml of BSA in each well. The attached particles were washed in a series of capture and release steps wherein the magnet pack is removed and the pin is raised and lowered to dislodge the SA-PMPs, and then the magnet pack is replaced to recapture the SA-PMPs. The wash plate was then removed and replaced with a GeNunc™ elution plate containing 20 µl of nuclease-free $H_2O$ in each well. The pin plate and magnet pack were lowered so that the pins were immersed. The magnet pack was removed and the particles dislodged as above, releasing the mRNA into solution. After 1 min., the magnet was returned to position atop the pin plate to collect the particles on the pins, typically about 2 min. The remaining solution contained purified mRNA.

EXAMPLE 3 mRNA Purification-Cell Sample

Test cells were suspended in GTC extraction buffer/BME at a concentration of $10^5$ cells per 20 µl. The cultured cells lysed spontaneously in the GTC buffer, thus no homogenization was required.

20 µl of sample solution were transferred to to a well of a multiwell plate, and the purification process was carried out as described in Example 2 hereinabove.

EXAMPLE 4

Single-stranded M13 Purification

200 µl of magnetically responsive particles coated with an oligonucleotide specific for M13 bacteriophage (Streptavidin MagneSphere™ Paramagnetic Particles, Promega Corporation, Madison, Wis., U.S.A.) were placed in a vial and washed three times with 0.1×SSC by repeatedly magnetizing and decanting the supernatant. After the final wash, the particles were then resuspended in 20 µl to prepare a 10x stock preparation.

2 µl (2 µg) of single-stranded M13 were transferred to each well of a multiwell plate. To each well of the multiwell plate, 50 µl of hybridization buffer containing 20% PEG 8000 and 2.5M NaCl and 180 µl of sterile water were added and mixed.

10 μl of 10×magnetically responsive particle stock were placed in each well of the plate, mixed and incubated for thirty minutes at 45° C.

The multiwell plate was then placed into the base of the magnetic separator of the present invention. The hinge pins of the pin plate were positioned in the channels of the hinges of the base and the pin plate was carefully lowered, immersing the pins into the wells of the microtiter plate. The external magnet pack was then placed on the top side of the pin plate, contacting the pin ends and the admixtures were incubated until the magnetic particles were cleared from the admixture, typically about 90 sec to 2 min.

The pin plate and magnet pack were then raised to about a 45° angle and the multiwell plate containing the admixture was removed and replaced with a fresh plate containing 200 μl of 0.1×SSC in each well and the particles were resuspended. This wash step was repeated three times. The final wash supernatant was removed as completely as possible, and the particles were resuspend in 30 μl of sterile water, and incubated for five minutes at 80° C. The particles were then magnetically separated as described hereinabove. The remaining solution contained the purified M13.

The purified M13 released from the particles was then electrophoresed with standards to confirm purification.

In summary, the present invention provides a simple, cost-effective device for effecting magnetic separation on multiple samples and facilitating processing steps on the magnetic particle-ligand complex.

While the present invention has now been described and exemplified with some specificity, those skilled in the art will appreciate the various modifications, including variations, additions, and omissions, that may be made in what has been described. Accordingly, it is intended that these modifications also be encompassed by the present invention and that the scope of the present invention be limited solely by the broadest interpretation that lawfully can be accorded the appended claims.

We claim:

1. A magnetic separation apparatus suitable for separating magnetic particles from a plurality of samples each containing the particles, the apparatus comprising:

a substantially non-magnetic separation chamber having a base and a plurality of containers disposed on said base in spaced-apart positions, each of said containers containing one of said samples;

a plurality of magnetic field directing elements, each said magnetic field-directing element having a longitudinal axis and opposed upper and lower ends, wherein each said container has one said lower end of a respective said element disposed therein for immersion into a respective said sample; and a permanent magnet means positioned externally of said containers and above the upper end of said elements, said magnet disposed and configured to generate magnetic flux lines collinear with said longitudinal axes of said elements to induce a magnetic field which, when said elements are immersed in said samples, attract said particles to said elements;

an element plate having a top side and a bottom side and a plurality of bores therethrough for receiving and holding said plurality of elements, said lower end of each of said elements projecting from the bottom of side of said element plate, said upper end of said elements projecting from said top side of said element plate.

2. The apparatus of claim 1, wherein said magnet means is adapted to be selectively removable from the upper end of said elements.

3. The apparatus of claim 1, wherein said magnet is superposed on said second ends of said elements.

4. The apparatus of claim 1, wherein said magnet means is a single, substantially planar magnet pack, said magnet pack being disposed substantially perpendicularly to said longitudinal axis of said elements on said top side of said element plate.

5. The apparatus of claim 4, wherein said magnet pack is an array of individual magnets.

6. The apparatus of claim 5, wherein, when said magnet pack is positioned on said top side of said element plate, four said elements being circumferentially proximate each magnet.

7. The apparatus of claim 5, wherein said array of magnets comprises 24 magnets and each said magnet has an energy strength of about 27M Gauss-Oersteds (MGO) to about 35 MGO.

8. The apparatus of claim 1, wherein each said element comprises a paramagnetic material.

9. The apparatus of claim 8, wherein said paramagnetic material is stainless steel.

10. The apparatus of claim 1, wherein each said element has a diameter of between about 0.5 mm and about 2 mm and a length of about 6 mm to 15 mm.

11. A method for magnetically separating a target substance from a test medium in a magnetic separation apparatus, the substance coupled to magnetically responsive particles, the apparatus comprising an array of nonmagnetic wells defining a separation chamber, nonmagnetic pins having a longitudinal axis and opposed upper and lower ends, a single substantially planar magnet pack for magnetizing the pins, the magnet pack capable of generating magnetic flux lines substantially collinear with said longitudinal axis, the method comprising the steps of:

(a) introducing said test medium into said wells;

(b) contacting a quantity of magnetically responsive particles comprising a receptor capable of binding specifically to said target substance in said test medium to produce target substance bearing particles;

(c) positioning the lower end of said pins within said wells;

(d) positioning said magnet pack above the upper end of said pins so that the plane of said magnet pack is substantially perpendicular to the longitudinal axis of said pins and (e) separating said target substance bearing particles from said test medium.

12. The method of claim 11, including the step of maintaining the magnetically responsive particles adhered to the magnetized pins within said container while removing the particles from the container.

13. The method of claim 11, including the step of washing the magnetically responsive particles adhered to the pins to remove residual test medium from the magnetically responsive particles and from the pins.

14. The method of claim 11, including the steps of:

removing said pins from said wells, wherein said magnetically responsive particles are adhered to the pins;

immersing said pins into a resuspension medium; and dislodging said particles from said pins into said resuspension medium by removing said magnet pack from the plane perpendicular to the longitudinal axis of said pins.

15. The method of claim 11, wherein the method is performed batchwise.

* * * * *